(12) United States Patent
Samson et al.

(10) Patent No.: US 6,673,040 B1
(45) Date of Patent: Jan. 6, 2004

(54) SYSTEM AND METHODS FOR CATHETER PROCEDURES WITH CIRCULATORY SUPPORT IN HIGH RISK PATIENTS

(75) Inventors: Wilfred J. Samson, Saratoga, CA (US); John A. Macoviak, La Jolla, CA (US)

(73) Assignee: Cardeon Corporation, Cupertino, CA (US)

( * ) Notice: Subject to any disclaimer, the term of this patent is extended or adjusted under 35 U.S.C. 154(b) by 0 days.

(21) Appl. No.: 09/384,467

(22) Filed: Aug. 27, 1999

Related U.S. Application Data

(63) Continuation-in-part of application No. 09/060,412, filed on Apr. 14, 1998, now Pat. No. 6,110,145, which is a continuation-in-part of application No. 08/632,883, filed on Apr. 16, 1996, now Pat. No. 5,738,649, and a continuation-in-part of application No. PCT/US97/06243, filed on Oct. 23, 1997.
(60) Provisional application No. 60/098,724, filed on Sep. 1, 1998.

(51) Int. Cl.$^7$ .............................................. A61M 29/00
(52) U.S. Cl. ............ 604/101.01; 604/509; 604/101.03; 604/101.05; 604/102.02; 604/919; 606/194
(58) Field of Search .......................... 604/96.01, 4.01, 604/6.14, 6.16, 27, 28, 48, 500, 507–510, 101.01, 101.03, 101.05, 102.02, 264, 523, 173, 528, 533, 912, 915, 919; 606/192, 194

(56) References Cited

U.S. PATENT DOCUMENTS 5,308,320 A 5/1994 Safar et al. ..................... 604/4

(List continued on next page.)

FOREIGN PATENT DOCUMENTS

EP 0 218 275 A 4/1987

(List continued on next page.)

OTHER PUBLICATIONS

Technical Specification Datascope Corp Percluder® Aortic Occluding Balloon. © 1987 Datascope Corp.

(List continued on next page.)

*Primary Examiner*—Manuel Mendez
*Assistant Examiner*—Cris L. Rodriguez
(74) *Attorney, Agent, or Firm*—Fulwider Patton Lee & Utecht, LLP

(57) ABSTRACT

A system and methods are described for performing catheter based procedures on high risk patients that mitigate the risk to the patient and extend the acceptable time window for response when emergencies or complications arise. The system is useful for stopped heart catheter procedures or as a safety backup in beating heart catheter procedures and is compatible with concurrent or sequential surgical interventions. The system combines a therapeutic or diagnostic catheter subsystem with a selective aortic perfusion and cardiopulmonary bypass subsystem. The catheter subsystem may include catheters for angioplasty, stent delivery, atherectomy, valvuloplasty or other diagnostic or therapeutic procedures. The selective aortic perfusion and cardiopulmonary bypass subsystem generally includes catheters and/or cannulas for draining blood from the patient's venous or arterial system, a perfusion pump, a blood oxygenator, at least one blood heat exchanger and catheters and/or cannulas for perfusing oxygenated blood into the patient's arterial system. The arterial perfusion catheters and/or cannulas are constructed with an upstream flow control member located in the patient's ascending aorta and a downstream flow control member located in the patient's descending aorta. The external flow control members may take the form of inflatable occlusion balloons and/or selectively deployable external catheter flow control valves. The external flow control members may be mounted on a single elongated catheter or cannula shaft or they may be mounted on separate catheter or cannula shafts for independent placement and deployment.

28 Claims, 7 Drawing Sheets

U.S. PATENT DOCUMENTS

| | | | | |
|---|---|---|---|---|
| 5,312,344 A | | 5/1994 | Grinfeld et al. | 604/101 |
| 5,368,555 A | | 11/1994 | Sussman et al. | |
| 5,451,207 A | | 9/1995 | Yock et al. | 604/53 |
| 5,458,574 A | * | 10/1995 | Machold et al. | 604/101.03 |
| 5,478,309 A | * | 12/1995 | Sweezer et al. | 604/509 |
| 5,695,457 A | | 12/1997 | St. Goar et al. | 604/4 |
| 5,738,649 A | * | 4/1998 | Macoviak | 604/43 |
| 5,762,624 A | | 6/1998 | Peters | 604/4 |
| 5,766,151 A | | 6/1998 | Valley et al. | 604/96 |
| 5,769,812 A | | 6/1998 | Stevens et al. | 604/4 |
| 5,906,588 A | * | 5/1999 | Safar et al. | 604/64 |
| 5,928,192 A | | 7/1999 | Maahs | 604/96 |
| 6,027,476 A | * | 2/2000 | Sterman et al. | 604/96.01 |
| 6,029,671 A | | 2/2000 | Stevens et al. | 128/898 |
| 6,059,757 A | * | 5/2000 | Macoviak et al. | 604/247 |
| 6,083,198 A | * | 7/2000 | Afzal | 604/101.01 |
| 6,083,215 A | * | 7/2000 | Milavetz | 604/509 |
| 6,090,096 A | * | 7/2000 | St. Goar et al. | 604/509 |
| 6,110,145 A | * | 8/2000 | Macoviak | 604/101.01 |
| 6,117,105 A | * | 9/2000 | Bresnaham et al. | 604/96.01 |
| 6,139,517 A | * | 10/2000 | Macoviak et al. | 604/8 |
| 6,152,141 A | * | 11/2000 | Stevens et al. | 128/898 |
| 6,267,747 B1 | * | 7/2001 | Samson et al. | 604/103.07 |
| 6,508,777 B1 | * | 1/2003 | Macoviak et al. | 604/4.01 |

FOREIGN PATENT DOCUMENTS

| | | |
|---|---|---|
| EP | 0 604 803 | 7/1994 |
| EP | 0 709 108 A | 5/1996 |
| WO | WO 95/32745 | 12/1995 |
| WO | WO 97/38748 | 10/1997 |
| WO | WO 97/48436 | 12/1997 |

OTHER PUBLICATIONS

Erath et al., "Balloon Catheter Occlusion of the Ascending Aorta," *Ann Thorac Surg*; 35:560–1 (1983).

Cosgrove DM, "Management of the Calcified Aorta: and Alternative Method of Occlusion," *Ann Thor Surg*; 36:718–719 (1983).

Leung WH. "Coronary and circulatory support strategies for percutaneous transluminal coronary angioplasty in high–risk patients." *Am Heart J*. 1993 Jun;125(6):1727–38.

Hirose, "Use of the Balloon Catheter for Distal Occlusion of the Aorta in Prosthetic Replacement of Aortic Arch Aneurysms." *Ann Thorac Surg*. 1985 Jun.;39(6):538–40.

Okita et al. "Utilization of Triple Lumen Balloon Catheter for Occlusion of The Ascending Aorta During Distal Aortic Arch Surgery With Hypothermic Retrograde Cerebral Circulation Technique Through Left Thorocotomy." *J. Card Surg*; 10:699–702 (1995).

Rubenstein et al. "Percutaneous Aortic Balloon Occlusion." *Surg Gynecol Obstet*; 164:561–563 (1987).

Robicsek, "Administration of Hypothermic Cardioplegia in the Presence of Aortic Regurgitation." *Ann Thorac Surg*. Feb;39(2):192–3 (1985).

Schwartz AE, Selective cerebral hypothermia by means of transfemoral internal carotid artery catheterization. *Radiology*. 1996 Nov;201(2):571–2.

Schwartz AE, "Isolated cerebral hypothermia by single carotid artery perfusion of extracorporeally cooled blood in baboons." *Neurosurgery*. 1996 Sep;39(3):577–81; discussion 581–2.

David P. Bichell, MD, et al., Axilloaxillary Cardiopulmonary Bypass: A Practical Alternative to Femorofemoral Bypass, © 1997 by The Society of Thoracic Surgeons Published by Elsevier Science Inc., Page(s) 702–705.

Joseph F. Sabik, MD, et al., Axillary Artery: An Alternative Site of Arterial Cannulation for Patients with Extensive Aortic and Peripheral Vascular Disease,© 1995 by Mosby–Year Book, Inc., The Journal of Thoracic and Cardiovascular Surgery, pp. 886–891.

Nicholas T. Kouchoukos, et al., Perfusion for Thoracic Aortic Surgery, Section V. Clinical Application and Management of CPB, pp. 636–654.

* cited by examiner

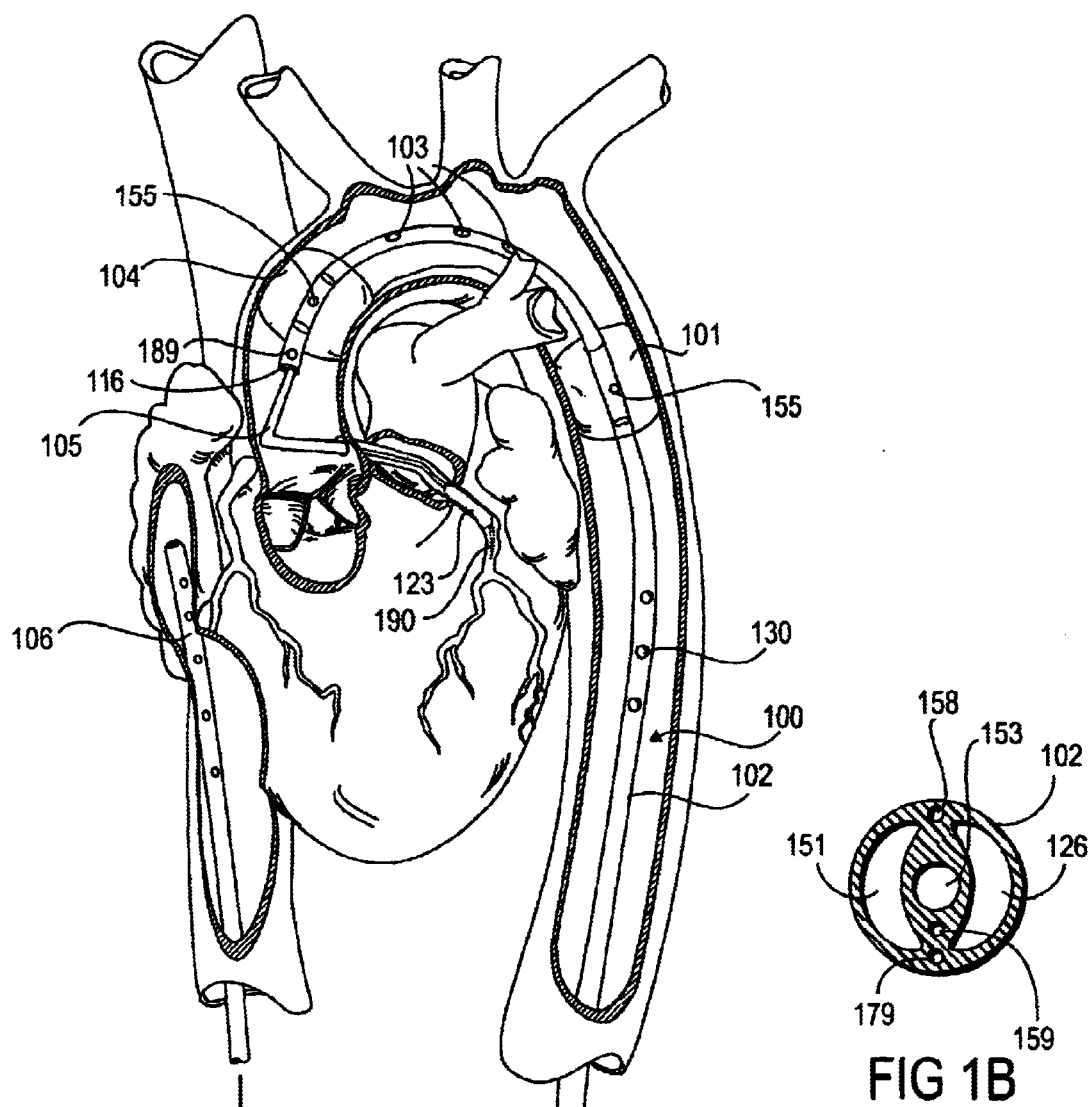
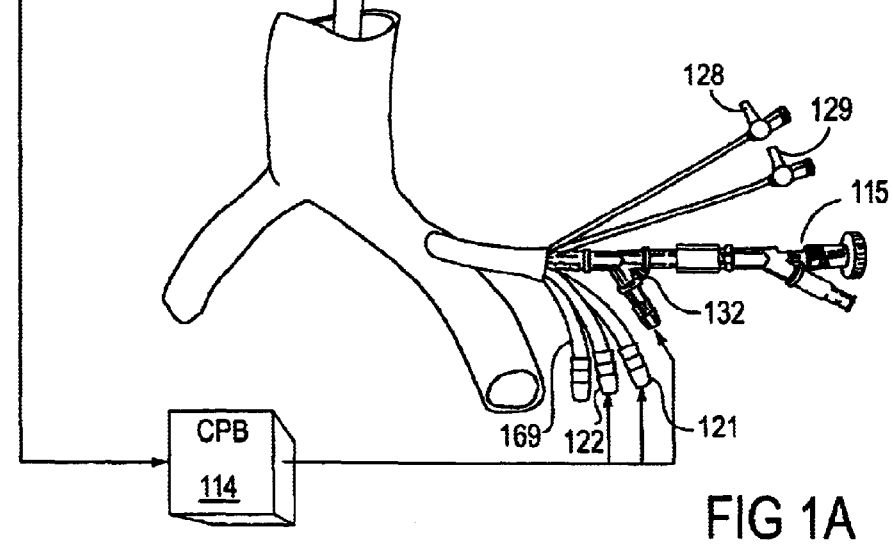
FIG 1B
FIG 1A

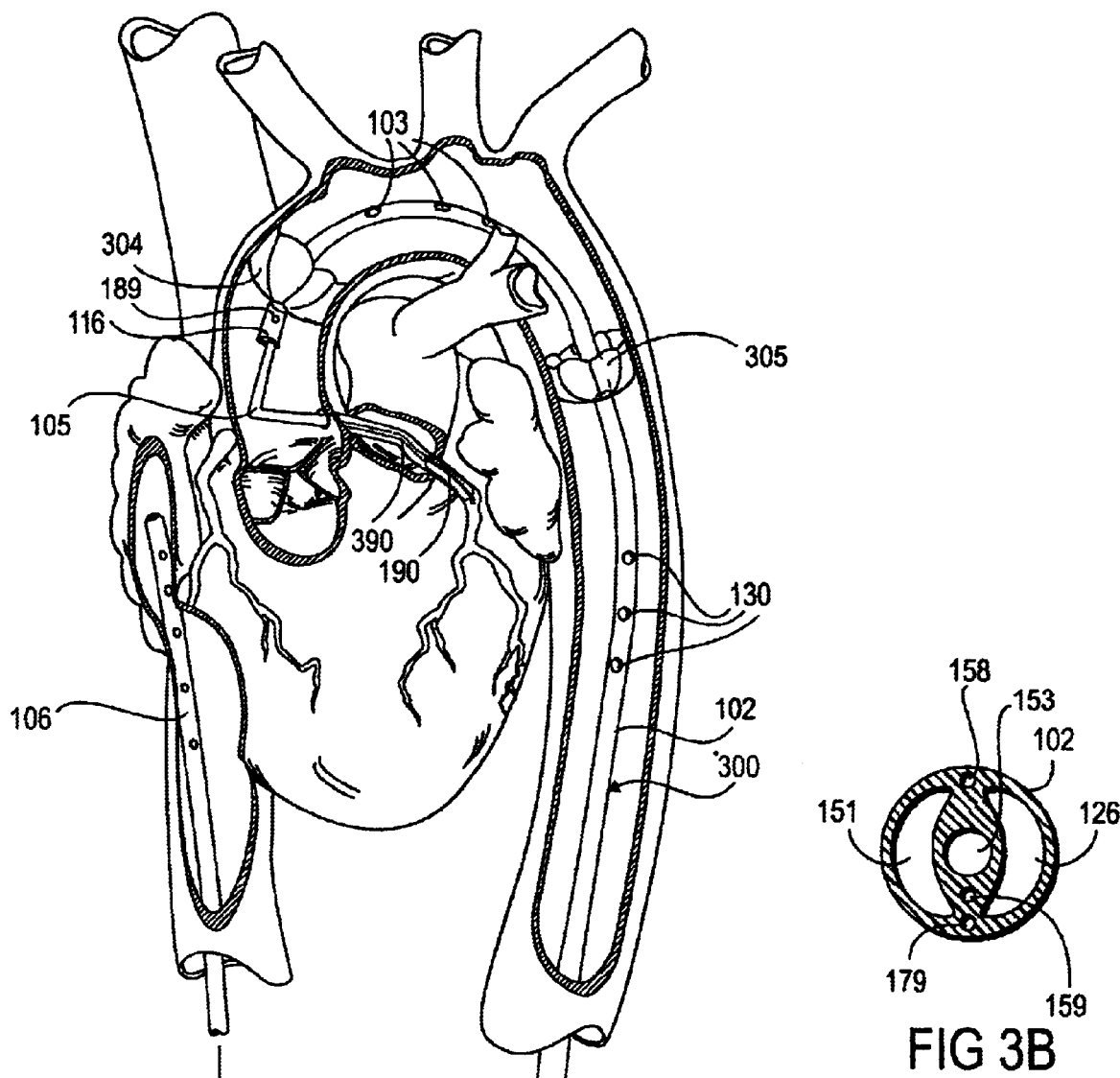
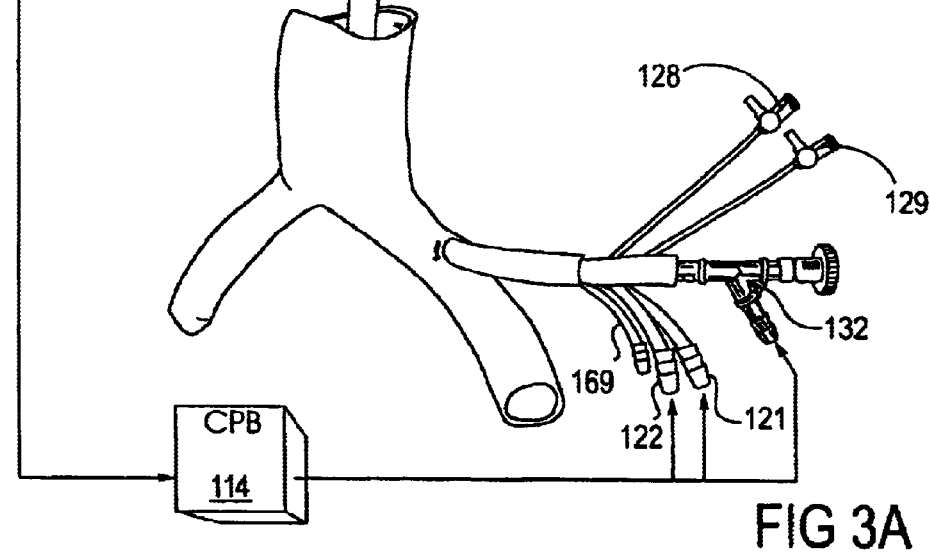
FIG 3B
FIG 3A

SYSTEM AND METHODS FOR CATHETER PROCEDURES WITH CIRCULATORY SUPPORT IN HIGH RISK PATIENTS

The present invention claims benefit and is a continuation-in-part application of application Ser. No. 09/060,412, filed Apr. 14, 1998, now U.S. Pat. No. 6,110,145, which is a continuation-in-part of application Ser. No. 08/632,883, filed Apr. 16, 1996 and PCT/US97/06243, filed Oct. 23, 1997, now U.S. Pat. No. 5,738,649 and claims benefit of U.S. Provisional Application No. 60/098,724, filed Sep. 1, 1998, now abandoned.

FIELD OF INVENTION

The present invention relates generally to cardiovascular catheters and also to circulatory support systems. More particularly, it relates to a system and method for performing catheter based medical procedures, such as balloon angioplasty, stent placement, atherectomy, valvuloplasty and other therapeutic procedures, with protective circulatory support in order to minimize the risk to the patient from such procedures. The system and methods of the present invention serve to expand the patient population treatable by catheter based procedures to include patients who might otherwise require open chest surgery with cardiopulmonary bypass and also to high risk patients who might not be acceptable candidates for these surgical alternatives.

BACKGROUND OF THE INVENTION

Many catheter based diagnostic and therapeutic procedures have been developed in the areas of interventional cardiology, interventional radiology, interventional neuroradiology and electrophysiology. Examples of such procedures include balloon angioplasty, stent placement, atherectomy and valvuloplasty. These and many other catheter based diagnostic and therapeutic procedures can benefit from the system and methods of the present invention, particularly in high risk patients.

Balloon angioplasty is a procedure in which a small, cylindrical balloon is mounted on an elongated catheter which is inserted into a stenosis or a narrowing in a blood vessel and inflated to dilate the stenosis and improve blood flow. Balloon angioplasty can be applied to coronary arteries, carotid arteries and peripheral arteries, as well as other body passages. Patents which describe apparatus and methods for performing balloon angioplasty include U.S. Pat. Nos. 4,195,637; 4,323,071; 4,545,390; 4,545,390; 4,538,622; 5,055,024; 4,490,421; 4,616,653; 5,133,364; 5,060,660; 5,031,636; 4,922,923; 4,917,103; 4,875,489; 4,827,941; 4,762,129; 4,988,356; 4;748;982; 5,040,548 and 5,061,2,73. The specifications of these patents and all other patents and patent applications mentioned herein are hereby incorporated by reference in their entirety.

Valvuloplasty is a closely related procedure in which a somewhat larger balloon or balloons are inserted into a stenosis in a heart valve and inflated to open the stenosis and improve blood flow through the valve. Valvuloplasty can be applied to the aortic valve, mitral valve, tricuspid valve or pulmonic valve. Patents which describe apparatus and methods for performing valvuloplasty include U.S. Pat. Nos. 4,787,388; 4,796,629; 4,909,252; 5,295,958.

Atherectomy is an alternative procedure to balloon angioplasty in which, rather than simply dilating the stenosis, some or all of the stenotic material is removed to debulk the stenosis and improve blood flow. Atherectomy includes both rotational atherectomy in which stenotic material is removed symmetrically about the catheter and directional atherectomy in which stenotic material is selectively removed from certain parts of the blood vessel. Patents which describe apparatus and methods for performing atherectomy include. U.S. Pat. Nos. 4,323,071; 5,071,425; 4,781,186; RE 33,569; 4,290,427; 4,315,511; 4,574,781; 4,621,636; 4,890,611; 5,368,603; 3,730,183; 5,071,424; 5,156,610; 5,282,484; 5,211,651; 5,267,955; 5,195,956; 5,178,625; 4,589,412; 4,854,325; 4,883,460; 4,273,128.

Stent placement, is a procedure often very closely associated with balloon angioplasty and also sometimes with atherectomy. Vascular stents, also known as endovascular prostheses, are small, generally cylindrical, metallic or polymeric scaffolds that are implanted within the lumen of a blood vessel to maintain patency of the lumen. Elective stent placement may be done as an adjunct to balloon angioplasty or atherectomy or emergency stent placement may be done in the case of a failed angoplas or atherectoiny. Stents can be applied to coronary arteries, carotid arteries and peripheral arteries, as well as other body passages. Stent grafts or covered stents resemble standard vascular stents with the addition of a prosthetic vascular wall over the metallic or polymeric scaffold of the stent. Patents which describe apparatus and methods for performing stent placement include. U.S. Pat. Nos. 5,041,126; 4,856516; 5,037,392; 5,683,452; 5,578,072; 5,571,171; 5,522,880; 5,360,443; 5,102,417; 4,776,337; 4,739,762; 4,733,665; 55674,278; 5,782,855; 5,780,807; 5,766,710; 5,766,239; 5,766,238; 5,759,192; 5,738,674; 5,735,893; 5,733,330; 5,728,158; 5,725,572; 5,725,549; 5,707,385; 5,700,286; 5,681,346; 5,649,977; 5,649,952; 5,637,113; 5,632,840; 5,629,077; 5,618,299; 5,607,444; 5,605,696; 5,603,721; 5,593,434; 5,591,197; 5,569,295; 5,556,413; 5,546,646; 5;514,154; 5,507,768; 5,498,240; 5,476,505; 5,458,615; 5,458,605; 5,456,667; 5,443,500; 5,443,458; 5,441,515; 5,437,083; 5,423,885; 5,421,955; 5,415,637; 5,409,495; 5,391,172; 5,360,401; 5,344,426; 5,242,399; 5,158,548.

Electrophysiology diagnostic studies and therapeutic ablation procedures are used for diagnosis and treatment of various cardiac arrhythmias. Patents that describe apparatus and methods for performing electrophysiology procedures include U.S. Pat. Nos. 4,699,147; 5,327,889; 4,960,134; 5,140,987; 4,522,212; 4,660,571; 4,664,120; 5,125,896; 5,104,393.

Other catheter based procedures will also benefit from the system and methods of the present invention, particularly in high risk patients. For example: transmyocardial revascularization, U.S. Pat. Nos. 4,658,817; 5,125,924; 5,125,926, patent ductus arteriosus closure, septal defect repair, U.S. Pat. Nos. 3,874,388; 4,874,089, intravascular ultrasonic imaging, U.S. Pat. Nos. 5,000,185; 4,794,931; 5,029,588; 4,024,234; 4,917,097; 5,167,233; 5,368,037; 5,190,046; WO 94/16625, laser angioplasty or ablation, U.S. Pat. Nos. 5,354,294; 5,366,456; 5,163,935; 4,740,047; 5,242,438; 5,147,353; 5,242,437; 5,188,634; 5,026,366; 4,788,975.

The system and methods of the present invention find particular use in performing catheter based medical procedures, such as balloon angioplasty, stent placement, atherectomy, valvuloplasty and other therapeutic procedures, on high risk patients. High risk patients in this context include extremely young or extremely elderly patients and patients whose cardiopulmonary functions are severely compromised.

In addition to the above examples, patients with severe cardiovascular disease or other complicating factors, such as patients requiring balloon angioplasty, stent placement or atherectomy in highly critical portions of the vasculature will particularly benefit from these procedures. Examples of highly critical portions of the vasculature may include: lesions in the ostia of the coronary arteries, the left main coronary artery, diseased saphenous vein grafts and totally occluded coronary arteries or the carotid arteries.

Because of the risks to the patient, the aforementioned catheter procedures are usually performed while a surgical backup team stands by on call with a surgical suite reserved for emergency surgery in the event that the procedure fails or if dangerous complications arise. This gives rise to two specific problems, surgical backup may not always be logistically possible and surgical backup is costly. One example of where surgical backup is not logistically possible, is when the catheter procedure is being performed in an emergency situation.

Surgical backup is also a significant economic burden for the patient, the hospital and the entire medical system. The timing for emergency surgery is very critical, although the surgical backup team only needs to be relied upon in a very small percentage of cases, it is necessary to have the surgical team and the operating room ready immediately. In particular, where a failed procedure results in severe complications, such as cardiac arrest, myocardial infarction or cerebral ischemia or embolization, there is only a narrow window of response time available to perform emergency surgery in order to save the patient.

Therefore, because of the conflicting pressures of economics and of patient safety, it would be extremely desirable to reduce the reliance on surgical backup for high risk catheter based procedures. The present invention is intended to provide a margin of protection that mitigates the risk to the patient and extends the acceptable time window for response when emergencies or complications arise.

Various strategies have been proposed to mitigate the danger to patients during high risk catheter procedures. These proposed strategies have include perfusion balloon catheters, intra-aortic balloon pumps, percutaneous or femoral-femoral cardiopulmonary bypass, retrograde coronary perfusion, and single-balloon intra-aortic occlusion catheters for cardioplegic arrest. None of these approaches provide all of the benefits of the present invention.

Perfusion balloon catheters, U.S. Pat. Nos. 5,573,508; 5,573,509; 5,344,402, are angioplasty catheters which have been adapted to provide blood flow downstream of the dilatation balloon to prevent ischemia of the myocardium during prolonged inflation of the balloon. This approach protects only the myocardium at risk of infarction downstream from the dilatation site. It does not provide global circulatory protection or selective cerebral protection in the event of low cardiac output or cardiac arrest. It also does not provide for elective cardiac arrest or a transition to cardiopulmonary bypass in the event that surgical intervention becomes necessary. Perfuision balloon catheters can be used in conjunction with the system and methods of the present invention.

Intra-aortic balloon pumps (IAPB) are balloon catheters that provide counterpulsation to reduce the cardiac pumping load and to augment coronary artery circulation. An IAPB only assists the beating heart in providing circulation and therefore would not provide global circulatory protection or selective cerebral protection in the event of cardiac arrest. An IAPB also does not provide for elective cardiac arrest or a transition to full cardiopulmonary bypass in the event that surgical intervention becomes necessary.

Percutaneous or femoral-femoral cardiopulmonary bypass, U.S. Pat. Nos. 3,513,845; 4,540,399; 5,0119469 is an approach to cardiopulmonary bypass (CPB) which uses peripherally inserted arterial and venous cannulas to avoid the necessity of a median sternotomy. This circulatory support method has been suggested for use in high risk angioplasty cases. However, this method affords no provision for safe, elective (e.g. cardioplegic) cardiac arrest, nor does it provide for prioritized cerebral protection.

Retrograde coronary perfusion or coronary retroperfusion (e.g. U.S. Pat. Nos. 5,451,207; 5,451,207; 5,655,548; 5,597,377; 5,533,957; 5,423,745; 5,401,244; 5,395,331; 5,324,260; 5,290,231; 5,059,167; 5,033,998; 5,024,668; 5,011,468; 4,934,996; 4,927,412; 4,917,667; 4,865,581; 4,850,969; 4,648,384; 4,459,977; 4,290,428) has been suggested for the treatment of myocardial ischemia, for myocardial protection during high risk catheter procedures and for administering cardioplegic arrest. For example, U.S. Pat. No. 5,451,207 describes the use of retrograde coronary perfusion for myocardial protection during a coronary atherectomy procedure. Retrograde coronary perfusion, however, requires additional cannulation in order to make the transition to cardiopulmonary bypass and it does not provide prioritized cerebral protection.

Single-balloon intra-aortic occlusion catheters, e.g. WO 96/30072, have been suggested for myocardial protection and for emergency or elective cardioplegic arrest during high risk catheter procedures. Single-balloon intra-aortic occlusion catheters of this type do not provide prioritized cerebral protection. U.S. Pat. No. 5,695,457 describes a system of coronary isolation catheters as a substitute for the single-balloon intra-aortic occlusion catheter for cardioplegia delivery and for use in high risk angiopiasty and other catheter procedures. This system also does not provide prioritized cerebral protection.

Another related technology involves cardiopulmonary support by selective aortic perfusion. U.S. Pat. Nos. 5,308,320, 5,383,854, 5,820,593 and 5,906,588 by Peter Safar, S. William Stezoski, and Miroslav Klain describe catheters that segment the aorta to perform differential perfusion. Other U.S. patent applications which address the concept of selective aortic perfusion include commonly owned, copending patent applications 08/909,293, filed Aug. 11, 1997; and 09/152,589 filed Aug. 11, 1998 to Safar et al.

Furthermore, U.S. Pat. Nos. 5,738,649, 5,827,237, 5,833,671; and commonly owned, copending patent applications 09/060,412, filed Apr. 14, 1998 by John A. Macoviak; and 08/665,635, filed Jun. 17, 1996; by John A. Macoviak and Michael Ross; and 60/067,945, filed Dec. 8, 1997, by Bresnahan et al. and 60/084,835, filed Apr. 25, 1997 by Macoviak et al. describe circulatory support systems and methods of use for isolated segmental perfusion. Perfusion shunt devices and deflectors for perfusing an isolated organ system while the beating heart supplies the remainder of the circulatory system are described in commonly owned, copending patent application 09/212,580, filed Dec. 14, 1998 and 60/116,836, filed Oct. 1, 1998 by Macoviak et al. In addition, commonly owned, copending patent application 09/306,555, filed May 6, 1999 by Macoviak et al. describes a circulatory support system and method of use for isolated segmental perfusion. These patent applications and all other patents referred to herein are hereby incorporated by reference in their entirety. Selective perfusion can be used to prioritize the flow of oxygenated blood or other protective fluids to the various organ systems, with different temperatures or compositions, for achieving optimal preservation of all organ systems within the body.

SUMMARY OF THE INVENTION

In keeping with the foregoing discussion, the present invention provides a system and methods for performing catheter based procedures on high risk patients that mitigate the risk to the patient and extend the acceptable time window for response when emergencies or complications arise. The system is useful in a number of operating modes, including: stopped heart catheter procedures, concurrent surgical interventions, sequential surgical interventions, catheter based interventions and as a safety backup or bail out system in beating heart catheter procedures. The system provides cardiopulmonary support for the patient's circulatory system and prioritized protection for the patient's cerebral and coronary circulation. The system, when used according to the methods of the present invention, allows a patient to be placed in varying degrees of suspended animation during the catheter procedure. Furthermore, when emergencies or complications arise, implementation of these procedures are intended to protect the patient's critical organ systems and to extend the safe period of time to initiate a surgical intervention.

The system combines a therapeutic or diagnostic catheter subsystem, which may take one of many known forms, with a selective aortic perfusion and cardiopulmonary bypass subsystem. The therapeutic or diagnostic catheter subsystem may take the form of an angioplasty subsystem, typically an angioplasty balloon catheter, a guiding catheter and a guidewire; a stent delivery subsystem, typically a stent delivery catheter, a stent, a guiding catheter and a guidewire; an atherectomy subsystem, typically an atherectomy catheter, a guiding catheter and a guidewire; a valvuloplasty subsystem, typically a valvuloplasty balloon catheter and a guidewire; or other known diagnostic or therapeutic catheter systems. The selective aortic perfusion and cardiopulmonary bypass subsystem generally includes catheters and/or cannulas for draining blood from the patient's venous or arterial system, a perfusion pump, a blood oxygenator, at least one blood heatexchanger and catheters and/or cannulas for perfusing oxygenated blood into the patient's arterial system. The arterial perfusion catheters and/or cannulas are especially configured to perform aortic segmentation and selective perfusion of the patient's circulatory system.

In order to accomplish aortic segmentation, the arterial perfusion catheters and/or cannulas are constructed with at least a first external flow control member and a second external flow control member. Additional external flow control members may be included if further segmentation of the circulatory system is desired. The external flow control members may take the form of inflatable occlusion balloons and/or selectively deployable external catheter flow control valves. The external flow control members may be mounted on a single elongated catheter or cannula shaft or they may be mounted on separate catheter or cannula shafts for independent placement and deployment.

When the arterial perfusion catheters and/or cannulas are deployed, the first external flow control member is positioned in the patient's ascending aorta between the coronary arteries and the brachiocephalic artery, and the second external flow control member is positioned in the patient's descending aorta downstream of the aortic arch. The external flow control members are used to control or to occlude fluid flow through the lumenof the aorta so that the aorta is divided into an ascending aorta or coronary artery segment, an aortic arch or cerebral blood flow segment and a descending aorta or corporeal blood flow segment. Each of these segments is perfusable separately or in combination. This may be accomplished by perfusion lumens within the same catheter or cannula shaft as the external flow control members are mounted on and/or through separate perfusion cannulas that are inserted into each segment. Each of the segments may be perfused with oxygenated blood and/or other fluids having a composition and/or temperature chosen for optimal preservation of the organ systems fed by the blood vessels branching from the segments.

In one particular embodiment of the system, the first and second external flow control members are mounted off the upstream and downstream ends of a perfusion shunt lumen, which allows blood flow from the heart to flow past the aortic arch without entering the arch vessels. An arch perfusion lumen allows selective perfusion of the arch vessels.

In some embodiments of the system, one or more of the components of the therapeutic catheter subsystem may be integrated with the components of the selective aortic perfusion and cardiopulmonary bypass subsystem to create a dual purpose device. For example, an angioplasty or atherectomy guiding catheter may be combined with two external flow control members to create a combined guiding catheter and aortic segmentation catheter.

When the system is used for performing stopped heart catheter procedures on a patient, cardiopulmonary bypass is established and the heart is stopped by elective cardiac arrest, for example by cardioplegic or hypothermic arrest. While the heart is stopped, each segment of the circulatory system is perfused with an, appropriate fluid to optimize preservation of the organs within each segment. The catheters of the therapeutic catheter subsystem are introduced either coaxially or in parallel with the aortic perfusion catheters or cannulas and the catheter procedure is performed while the heart is stopped. After the catheter procedure is complete, the heart is restarted and the patient is weaned off of bypass. Performing the catheter procedure while the heart is stopped significantly mitigates the risk to the patient from the catheter procedure or its possible complications.

When the system is used as a safety backup or bail out system while performing beating heart catheter procedures, the patient is cannulated and partial cardiopulmonary bypass may be initiated for circulatory support, but full cardiopulmonary bypass is not initiated. The catheters of the therapeutic catheter subsystem are introduced either coaxially or in parallel with the aortic perfusion catheters or cannulas and the catheter procedure is performed in the normal manner while the heart is still beating. If the catheter procedure is successful and there are no complications, the patient is extubated at the end of the procedure and sent to the recovery room. However, if emergencies or complications arise during the catheter procedure, full cardiopulmonary bypass can be established immediately by simply stepping up the flow rate of the perfusion pump. In addition, selective aortic perfusion can be performed by deploying the external flow control members enabling the segmentation of the aorta whereby each segment can be perfused with a separate protective fluid. Through this method, the patient can be placed in varying degrees of suspended animation protecting the affected organ systems until an emergency surgical intervention can be performed. The different degrees of suspended animation include: partial bypass for circulatory support, full cardiopulmonary bypass and elective cardiac arrest, neuroplegic arrest, with or without elective cardiac arrest, and complete hypothermic circulatory arrest. The patient can be kept in the selected degree of suspended animation while the surgical team is assembled and while the operating room is being prepared or while the patient is being transferred to another facility with the necessary surgical resources.

The system may also be used for performing catheter procedures on a patient in conjunction with elective surgical interventions. For example angioplasty, stenting or atherectomy can be performed in conjunction with coronary artery bypass or cardiac valve replacement surgery. The catheter procedures may be performed concurrently with the surgical interventions while the heart is stopped or they can be performed sequentially before or after the surgical interventions while the heart is stoppe,d or while it is beating. If the catheter procedure is performed while the heart is beating, the selective aortic perfusion and cardiopulmonary bypass subsystem will be used as a safety backup system during the catheter procedure, as described above.

BRIEF DESCRIPTION OF THE DRAWINGS

FIG. 1A shows a first embodiment of the system for performing catheter based medical procedures with protective circulatory support having a dual-balloon selective arterial perfusion cannula.

FIG. 1B is a cross section view of the catheter shaft of the aortic catheter of FIG. 1.

FIG. 3A shows a third embodiment of the system for performing catheter based medical procedures with protective circulatory support having a selective arterial perfusion cannula with first and second selectively deployable external catheter flow control valves.

FIG. 3B is a cross section view of the catheter shaft of the aortic catheter of 3A.

DETAILED DESCRIPTION OF THE INVENTION

Figure 2:
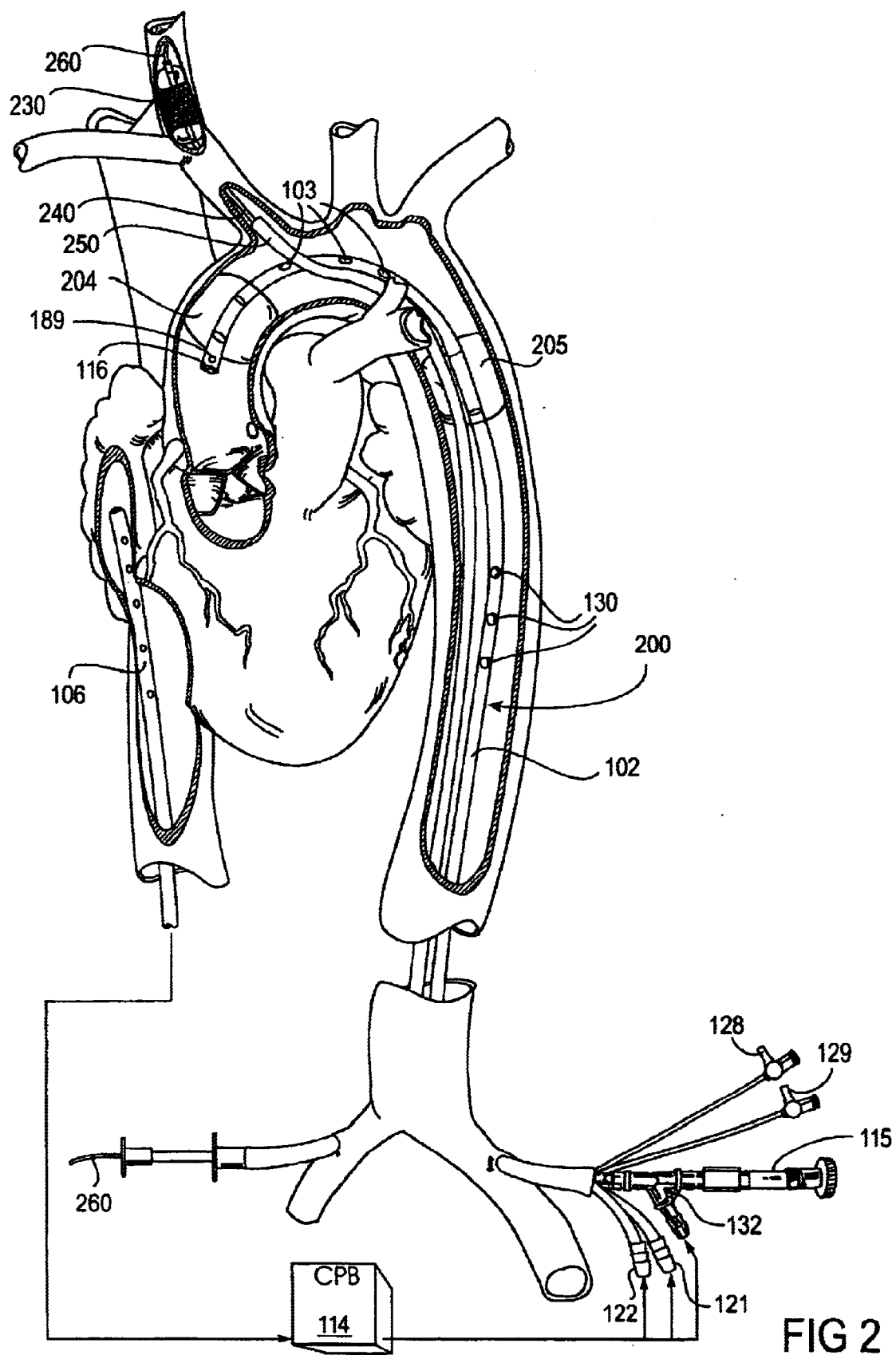
FIG. 2 shows a second embodiment of the system for performing catheter based medical procedures with protective circulatory support having a dual-balloon selective arterial perfusion cannula and a contralateral therapeutic catheter subsystem.

Referring now to the figures where like reference numbers refer to similar components or features, FIG. 1A shows a first exemplary embodiment of the system for performing catheter based medical procedures with protective circulatory support in high risk patients. The system of FIG. 1A uses a dual-balloon selective arterial perfusion cannula similar to those described in U.S. Pat Nos. 5,308,320, 5,383,854, 5,820,593 and 5,906,588 and in commonly owned, copending patent applications 08/909,293, 09/152, 589 and 09/205,753, which have previously been incorporated by reference. The dual balloon selective arterial perfusion cannula is modified for this application by making the distal perfusion lumen with sufficient internal diameter to accommodate the catheters of the therapeutic catheter subsystem.

The system of FIG. 1A includes a venous cannula 106 that is inserted into a large vein of the patient's circulatory system, such as the inferior or superior vena cava, the femoral vein or the jugular vein, and/or into the right ventricle. The venous cannula 106 mnay be inserted through a peripheral venous access, such as through the femoral vein or the jugular vein, or through a central access into the inferior or superior vena cayva or the right ventricle. The venous cannula 106 has at least one drainage lumen for draining venous blood from the patient. The drainage lumen of the venous cannula 106 is connected by way of connector tubing to a cardiopulmonary support system 114. The cardiopulmonary support system 114 typically includes a venous blood reservoir, a blood oxygenator, a perfusion pump and at least one blood heat exchanger and a cardioplegia source. The output of the cardiopulmonary support system 114 is connected to the double-balloon selective aortic perfusion cannula 100.

The dual-balloon, selective arterial perfusion cannula 100 is configured for retrograde introduction into the patient's aorta via a peripheral arterial access point, such as the femoral artery. Referring to FIG. 1B the dual-balloon, selective artermal perfusion cannula 100 has a tubular shaft 102 that includes an arch perfusion lumen 126, a cardioplegia or distal perfusion lumen 153, upstream and downstream balloon inflation luimens 158 and 159, alternatively one lumen may be used, and optionally, a corporeal perfusion lumen 151 and a root pressure lumen 179. A first, upstream occlusion balloon 104 or other expandable occlusion member is mounted on the tubular shaft 102 so that it is positioned in the ascending aorta between the coronary arteries and the right brachiocephalic artery. A second, downstream occlusion balloon 101 or other expandable occlusion member is mounted on the tubular shaft 102 so that it is positioned in the descending aorta downstream of the left subclavian artery. The optional corporeal perfusion lumen 151 extends through the tubular shaft 102 from a corporeal perfusion fitting 121 on the proximal end of the catheter 100 to one or more corporeal perfusion ports 130 on the tubular shaft 102 proximal to the downstream occlusion balloon 101.

If the catheter 100 is constructed without the optional corporeal perfusion lumen 151, corporeal perfusion can be provided through a coaxial, collateral or contralateral perfusion cannula. The arch perfusion lumen 126 extends through the tubular shaft 102 from an arch perfusion fitting 122 on the proximal end of the catheter 100 to one or more arch perfusion ports 103 on the tubular shaft 102 between the upstream occlusion balloon 104 and the downstream occlusion balloon 101.

The cardioplegia or distal perfusion lumen 153 extends through the tubular shaft 102 from a cardioplegia fitting 132 on the proximal end of the catheter 100 to one or more cardioplegia ports 116 on the tubular shaft 102 distal to the upstream occlusion balloon 104. The cardioplegia fitting also includes a Touhy-Borst compression fitting 115 or other suitable hemostasis valve configured for receiving a second medical instrument and creating a fluid tight seal. The distal perfusion lumen 153 is made with an, internal diameter sufficient to accommodate the catheters of the therapeutic catheter subsystem as well as fluid delivery. Optionally, the arterial catheter may also include a root pressure lumen 179 that extends through the tubular shaft 102 from a pressure fitting 169 on the proximal end of the catheter 102 to a pressure port 189 on the tubular shaft distal to the upstream occlusion balloon. A common balloon inflation lumen or separate balloon inflation lumens 158 and 159 extend through the tubular shaft from one or more balloon inflation fittings 128 and 129 on the proximal end of the cannula to balloon inflation ports 155 within the upstream occlusion balloon 104 and the downstream occlusion balloon 101.

The system includes a therapeutic catheter subsystem, which may take one of many known forms. In this illustrative embodiment, the system is shown with a coronary angioplasty subsystem, including an angioplasty balloon catheter 123, a guiding catheter 105 and a guidewire 190. In similar exemplary embodiments, the, system may include a coronary stent placement subsystem, a coronary atherectomy subsystem using a directional or rotational atherectomy catheter, an aortic or mitral valvuloplasty subsystem or other known therapeutic catheter system.

Angioplasty guiding catheters are typically made with an external diameter between 6 and 9 French (approximately 2–3 mm outside diameter), whereas atherectomy guiding catheters are typically made with an external diameter between 6 and 12 French (approximately 2–4 mm outside diameter). The distal perfusion lumen 153 of the dual-balloon, selective arterial perfusion cannula 100 should be made with an internal diameter sufficient to accommodate the chosen guiding catheter with additional clearance for easy insertion and manipulation of the guiding catheter. In addition, the distal perfusion lumen 153 may be lined with a lubricious material, such as a fluoropolymer like PTFE, to facilitate. insertion and manipulation of the guiding catheter. Alternatively, the guiding catheter of the angioplasty subsystem may be integrated into the dual-balloon, selective arterial perfusion cannula 100 to create a combined dual-purpose device. A Y-fitting 115 with a hemostasis valve or Touhy-Borst compression fitting is provided at the proximal end of the distal perfusion lumen 153 of the dual-balloon, selective arterial perfusion cannula 100 to allow insertion and withdrawal of the therapeutic catheter subsystem without excessive bleeding or leaking of perfusate.

FIG. 2 shows a second exemplary embodiment of the system for performing catheter based medical procedures with protective circulatory support in high risk patients. The system of FIG. 2 uses a dual-balloon selective arterial perfusion cannula 200 similar in many ways to the cannula 100 described above in connection with FIG. 1A. However, in this embodiment the therapeutic catheter subsystem is inserted into the contralateral femoral artery and advanced through the aorta in parallel with the dual-balloon selective arterial perfusion cannula 200. Possible modifications to the dual-balloon, selective arterial perfusion cannula 100 of FIG. 1A for this embodiment of the system include elimination of the Y-fitting and possible reduction of the internal diameter of the distal perfusion lumen since it is not required to accommodate the catheters of the therapeutic catheter subsystem.

Again, the therapeutic catheter subsystem may take one of many possible forms. For example, when used in combination with a coronary angioplasty, stent placement or atherectomy subsystem, the guiding catheter 250 is advanced through the aorta parallel with the dual-balloon selective arterial perfusion cannula 200. If the system is being used as a safety backup system in beating heart catheter procedures, the first 204 and second aortic occlusion balloons 205 of the dual-balloon selective arterial perfusion cannula need not be inflated initially. If it is deemed necessary to make a transition to a stopped heart procedure, either electively or in the event of an emergency, the first 204 and second 205 aortic occlusion balloons are inflated to occlude the aortic lumen. The guiding catheter 250 is sealed between the inflated second balloon 205 and the aortic wall. This does not interfere with the ability of the second occlusion balloon 205 to segment the aortic lumen.

This embodiment of the system is particularly useful for procedures, such as carotid angioplasty and carotid stent placement, where the therapeutic catheter subsystem is not required to extend all the way through the dual-balloon selective arterial perfusion cannula 200. FIG. 2 illustrates the use of the system with a carotid stent placement subsystem, including a stent placement catheter 240, a stent 230, a guiding catheter 250 and a guidewire 260. The guiding catheter 250 parallels the dual-balloon selective arterial perfusion cannula 200 until it reaches the aortic arch, at which point, it branches off selectively or subselectively into the left or right carotid artery. The stent placement catheter 240 is advanced through the guiding catheter 250 to place the stent 230 in the carotid artery. If it is deemed necessary to make a transition to a stopped heart procedure, either electively or in the event of an emergency, the first 204 and second 205 aortic occlusion balloons are inflated to occlude the aortic lumen. The guiding catheter 250 is sealed between the second balloon 205 and the aortic wall. This configuration is particularly useful for selectively delivering prioritized perfusion and/or neuroprotective agents (e.g. neuroplegic agents) to the cerebral circulation to prevent neuronal damage from hypoperfusion or embolization that may result from carotid catheter procedures, including angioplasty, atherectorny or stent placement.

In an alternative embodiment to FIG. 1A or FIG. 2, the dual-balloon selective arterial perfusion cannula may be constructed with the arch perfusion lumen being of sufficient internal diameter to accommodate the guiding catheter of a carotid angioplasty or stent placement subsystem and having a catheter exit port located in the aortic arch between the first and second occlusion balloons.

FIG. 3A shows a third exemplary embodiment of the system for performing catheter based medical procedures with protective circulatory support in high risk patients. The system of FIG. 3A uses a selective arterial perfusion cannula 300 having first 304 and second 305 external flow control members in the form of selectively deployable external catheter flow control valves. External catheter valves suitable for use as external flow control members are described in U.S. Pat Nos. 5,833,671 and 5,827,237 as well as commonly owned, copending U.S. patent application Ser. No. 08/665,635 which are hereby incorporated by reference in their entirety.

The dual-valve, selective arterial perfusion cannula 300 is configured for retrograde introduction into the patient's aorta via a peripheral arterial access point, such as the femoral artery. Referring to FIG. 3B, the dual-valve, selective arterial perfusion cannula 300 has a tubular shaft 102 that includes an arch perfusion lumen 126, a cardioplegia or distal perfusion lumen 153, one or two valve actuation members and/or lumens 158 and 159 and, optionally, a corporeal perfusion lumen 151 and a root pressure lumen 179. A first, upstream external catheter flow control valve 304 is mounted on the tubular shaft 102 so that it is positioned in the ascending aorta between the coronary arteries and the right brachiocephalic artery. A second, downstream external catheter flow control valve 305 is mounted on the tubular shaft so that it is positioned in the descending aorta downstream of the left subclavian artery. In one particularly preferred embodiment, the first, upstream external catheter flow control valve 304 is an antegrade valve that allows greater fluid flow in the antegrade direction than in the retrograde direction, and the second, downstream external catheter flow control valve 305 is a retrograde valve that allows greater fluid flow in the retrograde direction than in the antegrade direction. The optional corporeal perfusion lumnen 151 extends through the tubular shaft 102 from a corporeal perfusion fitting 121 on the proximal end of the catheter 300 to one or more corporeal perfusion ports 130 on the tubular shaft 102 proximal to the downstream occlusion valve 305.

If the cannula 300 is constructed without the optional corporeal perfusion lumen 151, corporeal perfusion can be provided through a coaxial or collateral perfusion carnula. The arch perfusion lumen 126 extends through the tubular shaft 102 from an arch perfusion fitting 122 on the proximal end of the catheter 300 to one or more arch perfusion ports 103 on the tubular shaft 102 between the upstream occlusion valve 304 and the downstream occlusion valve 305. The cardioplegia or distal perfusion lumen 153 extends through the tubular shaft 102 from a cardioplegia fitting 132 on the proximal end of the catheter to one or more cardioplegia ports 116 on the tubular shaft 102 distal to the upstream occlusion valve 304. The distal perfusion lumen 153 is made with an internal diameter sufficient to accommodate the catheters of the therapeutic catheter subsystem as well as the ability to deliver fluid therethrough. Optionally, the arterial cannula may also include a root pressure lumen 179 that extends through the tubular shaft from a pressure fitting 169 on the proximal end of the catheter to a pressure port 189 on the tubular shaft distal to the upstream occlusion valve 304.

The therapeutic catheter subsystem may take one of many possible forms. By way of example, the system of FIG. 3A is shown with a coronary atherectomy subsystem, including an atherectomy catheter 390, a guiding catheter 105 and a guidewire 190. The distal perfusion lumen 153 of the dual-valve, selective arterial perfusion cannula 300 should be made with an internal diameter sufficient to accommodate the chosen guiding catheter 105 with additional clearance for easy insertion and manipulation of the guiding catheter 105 as well as delivery of fluid. In addition, the distal perfusion lumen 153 may be lined with a lubricious material, such as a fluoropolymer like PTFE, to facilitate insertion and manipulation of the guiding catheter 105. Alt&rnatively, the guiding catheter 105 of the angioplasty subsystem may be integrated into the dual-valve, selective arterial perfusion cannula 300 to create a combined dual-purpose device. A Y-fitting with a hemostasis valve 1132 or compression fitting is provided at the proximal end of the distal perfusion lumen 153 of the dual-valve, selective arterial perfusion cannula 300 to allow insertion and withdrawal of the therapeutic catheter subsystem without excessive bleeding or leaking of perfusate.

Alternatively, dual-valve, selective arterial perfusion cannula 300 can be constructed without the Y-fitting and hemostasis valve and with a smaller diameter distal perfusion lumen for operating the system by the method described above in connection with FIG. 2.

Figure 4:
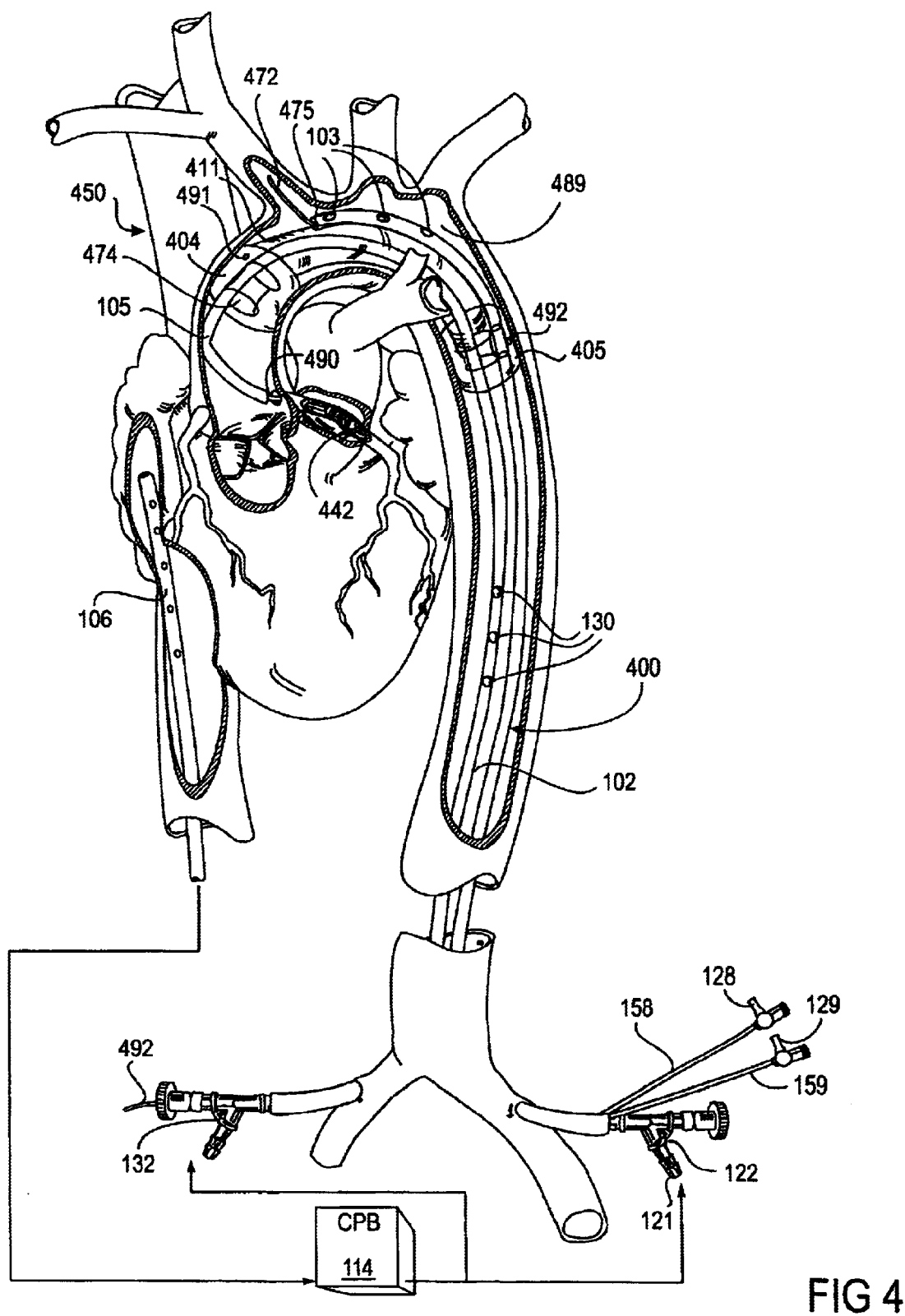
FIG. 4 shows a fourth embodiment of the system for performing catheter procedures with a perfusion shunt device for selective perfusion of a patient's cerebral circulation and upper extremities, while the beating heart supplies the viscera and lower extremities with blood.

FIG. 4 shows a fourth embodiment of the system for performing catheter procedures in high risk patients using a perfusion shunt device 450, mounted on a selective arterial perfusion cannula 400, for selective perfusion of a patient's cerebral circulation and upper extremities, while the beating heart supplies the viscera and lower extremities with blood. Suitable perfusion shunt devices 450 for this application are described in detail in commonly owned, copending patent application 60/069,470, filed Dec. 15, 1997 and corresponding utility application 09/212,580 filed Dec. 14, 1998 by Macoviak et al., which are hereby incorporated by reference in their entirety. The system of FIG. 4, includes a venous cannula 106 that is inserted into a large vein of the patient's circulatory system and connected by way of connector tubing to a cardiopulmonary support system 114. Oxygenated blood from the output of the cardiopulmonary support system 114 is directed to an arch perfusion lumen of the perfusion shunt device 450 and out the arch perfusion ports 103.

In a simplified version of this embodiment, the venous cannula 106 can be replaced by an arterial drainage cannula for draining oxygenated blood from the patient. A perfusion pump redirects the oxygenated blood through an optional heat exchanger to cool or warm the blood, then to an arch perfusion lumen of the perfusion shunt device. This embodiment of the system avoids the complexity of a blood oxygenator by using the patient's own lungs to supply oxygenated blood to the arch perfusion lumen. This simplified version of the system cannot be used for complete cardiopulmonary bypass.

The arch perfusion shunt device 450 has an expandable shunt conduit 411 mounted on an elongated catheter shaft 102. The expandable shunt conduit 411 has an upstream sealing member 404 at the upstream end of the conduit 411 and a downstream sealing member 405 at the downstream end of the conduit 411. The upstream and downstream sealing members 404 and 405 may be inflatable, toroidal balloons, as illustrated, or external flow control valves may be used. A common inflation lumen or separate inflation lumens 158 and 159 extend through the catheter shaft 102 from one or more inflation; fittings 128 and 129 on the proximal end of the catheter 400 to inflation ports 491, 492 within the upstream sealing member 404 and the downstream sealing member 405. The expandable shunt conduit 411 is inserted into the patient's aorta in a collapsed state and is expanded within the aortic arch with the inflated upstream sealing member 404 positioned between the aortic valve and the brachiocephalic artery and the inflated downstream sealing member 405 positioned downstream of the left subclavian artery. An arch perfusion lumen within the catheter shaft extends from a perfusion fitting 122 at the proximal end of the catheter shaft to one or more arch perfusion ports 103 within the annular chamber 489 surrounding the shunt conduit 411. Optionally, the arch perfusion shunt device 450 may also include a shunt conduit lumen occlusion balloon for converting the patient to full cardiopulmonary bypass with cardioplegic arrest.

The system includes a therapeutic catheter subsystem, for example a coronary stent placement subsystem is illustrated, including a stent placement catheter 490, which may be an angioplasty balloon catheter, a guiding catheter 105 and a guidewire 442. The therapeutic catheter subsystem may also take the form of a coronary or carotid angioplasty, stent placement or atherectomy subsystem, an aortic or mitral valvuloplasty subsystem or other known therapeutic catheter system. The catheters of the therapeutic catheter subsystem may be placed through the lumen of the shunt conduit 474, as illustrated, particularly for catheter procedures in the heart or the coronary arteries.

Alternatively, the catheters of the therapeutic catheter subsystem may be placed exterior to the shunt conduit 411. This configuration is particularly useful when the perfusion shunt device 450 is being used as a safety backup in beating heart catheter procedures or when performing carotid procedures.

In another alternative construction, the perfusion shunt device 450 may be constructed with the arch perfusion lumen being of sufficient internal diameter to accommodate the guiding catheter 472 of a carotid angioplasty or stent placement subsystem and having a catheter exit port 475 located in the aortic arch between the upstream 404 and downstream sealing members 405.

Furthermore, a corporeal perfusion lumen connected to corporeal perfusion ports 130 may be provided either through the therapeutic catheter subsystem as depicted or through the selective arterial perfusion cannula 400 by adding an additional corporeal lumen to either to make the system completely compatible for emergency bypass. Alternatively, a separate contralateral or collateral cannula may be used independently.

Figures 5A, 5B:
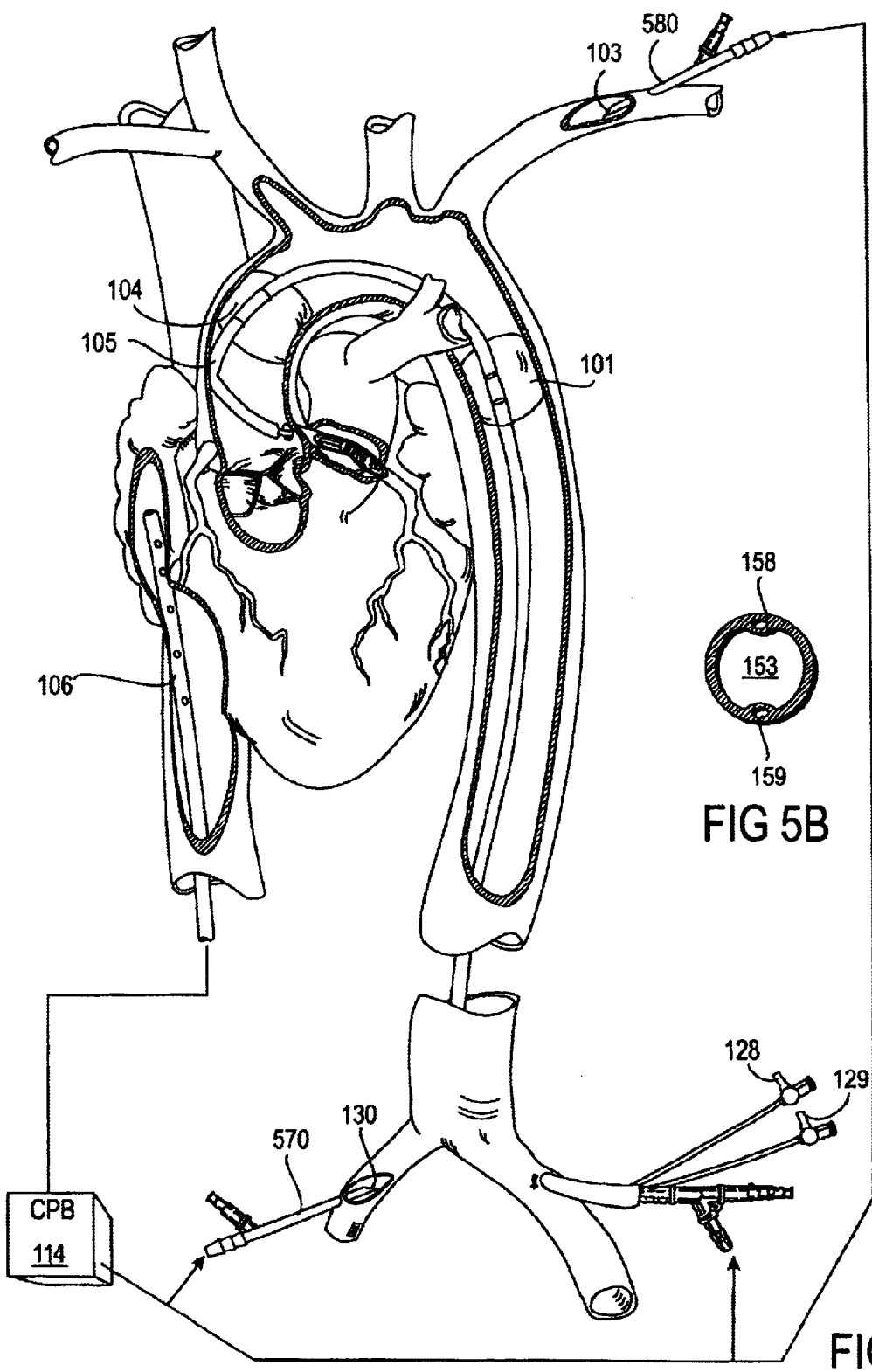
FIG. 5A shows an alternative embodiment of the system for performing catheter procedures, wherein the therapeutic catheter subsystem includes a guiding catheter having first and second external flow control members in the form of inflatable occlusion balloons or selectively deployable external catheter flow control valves.
FIG. 5B is a cross section view of the catheter shaft of the aortic catheter of FIG. 5A.

FIG. 5A shows an alternative embodiment of the system of the present invention. In this embodiment, the therapeutic catheter subsystem includes a guiding catheter 105 having a first 104 and a second 101 external flow control member in the form of inflatable occlusion balloons, as illustrated, or of selectively deployable external catheter flow control valves. Referring to FIG. 5B the guiding catheter 105 has an elongated tubular shaft 102 with a central instrument lumen 153 and one or two balloon inflation lumens 158 and 159 or valve actuation lumens. The main aortic catheter of the selective aortic perfusion and cardiopulmonary bypass subsystem is eliminated.

The aortic segmentation function of the aortic catheter is fulfilled by the first 104 and second 101 external flow control members on the guiding catheter 105. The perfusion functions are fulfilled by a first peripheral arterial cannula 570 placed in a lower extremity, for example in the femoral artery and a second peripheral arterial cannula 580 that is placed in an upper extremity, for example in the left or right subelavian or axillary artery and by the central instrument lumen 153 of the guiding catheter. The first peripheral arterial cannula 570 supplies oxygenated blood to the corporeal circulation, the second peripheral arterial cannula 580 supplies oxygenated blood and/or neuroprotective agents to the cerebral circulation. The central instrument lumen 153 of the guiding catheter 105 can be used to deliver oxygenated blood and/or cardioplegic and/or protective agents to the coronary circulation.

Figure 6:
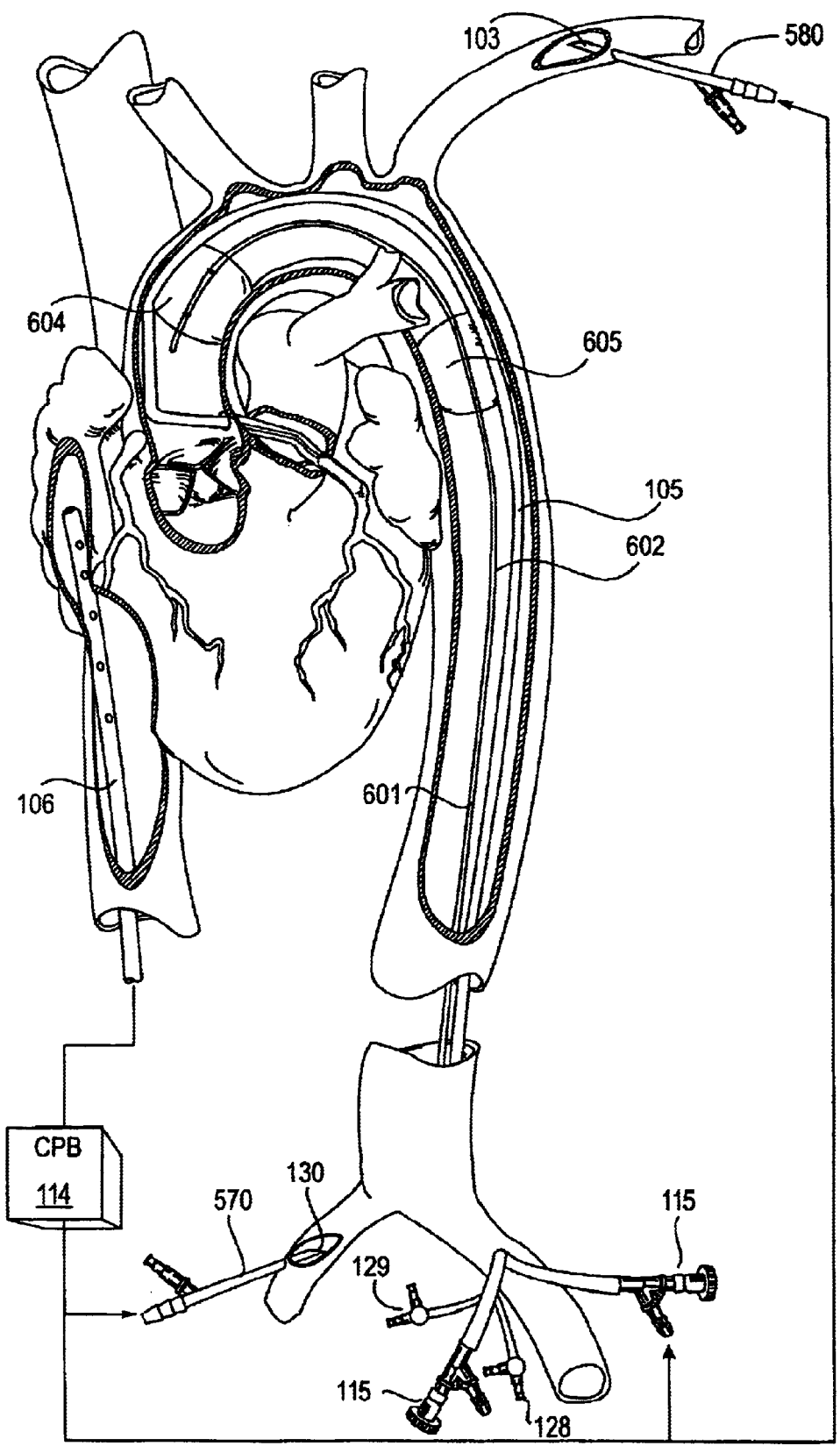
FIG. 6 shows another alternative embodiment of the system for performing catheter procedures with a low profile dual-balloon occlusion catheter having a first and a second external flow control member in the form of inflatable occlusion balloons or selectively deployable external catheter flow control valves.

FIG. 6 shows, another alternative embodiment of the system of the present invention. In this embodiment, the main aortic catheter of the selective aortic perfusion and cardiopulmonary bypass subsystem has been replaced with a low profile dual-balloon occlusion catheter 601 having a first 604 and a second external flow control members 605 in the form of inflatable occlusion balloons, as illustrated, or of selectively deployable external catheter flow control valves.

The low profile dual-balloon occlusion catheter 601 is placed in parallel with the guiding catheter 105 of the therapeutic, catheter subsystem. The low profile dual-balloon occlusion catheter 601 has an elongated catheter shaft 602 having one or two balloon inflation or valve actuation lumens and, optionally, a guidewire lumen. Alternatively, the elongated catheter shaft 602 may be constructed similar to a guidewire body with no additional lumens for easy insertion and extremely low profile.

The aortic segmentation function of the system is fulfilled by the first 604 and second 605 external flow control members on the low profile dual-balloon occlusion catheter 601, and the perfusion functions are fulfilled by a first peripheral arterial cannula 570 placed in a lower extremity, for example in the femoral artery, and the second peripheral arterial cannula 580 that is placed in an upper extremity, for example in the left or right subclavian or axillary artery and or by the instrument lumen of the guiding catheter.

The first peripheral arterial cannula 570 supplies oxygenated blood to the corporeal circulation, the second peripheral arterial cannula 580 supplies oxygenated blood and/or neuroprotective agents to the cerebral circulation, and the instrument lumen of the guiding catheter 105 can be used to deliver cardioplegic and/or protective agents to the coronary circulation. The extreme low profile of the low profile dual-balloon occlusion catheter 601 makes it especially useful as an emergency bail out catheter because it can be placed through an existing arterial access site or introducer sheath, and the peripheral arterial cannulas and the venous cannula can be placed percutaneously to quickly initiate cardioplegic arrest and/or selective cerebral perfusion in the event of an unforeseen complication during a catheter based procedure.

Although the examples given include many specific uses, they are intended as illustrative of only some of the possible embodiments of the invention. Other embodiments and modifications will, no doubt, occur to those skilled in the art. For example, each of the aortic catheters or cannulas of the system can be configured for peripheral placement via the subclavian or axillary artery or for central placement via an aortotomy incision, as described in conmmonly owned, copending patent application 60/067,945 and the corresponding utility application 09/205,753 filed Dec. 4, 1998 which are hereby incorporated by reference in their entirety. In addition, the functions of the aortic catheters or cannulas of the system can be replaced by two or more separate catheters with the first and second flow control members mounted thereon, as described in commonly owned, copending patent application 60/084,835 and the corresponding utility application 09/306,555 filed May 6, 1999 which are hereby incorporated by reference in their entirety.

Figure 7:
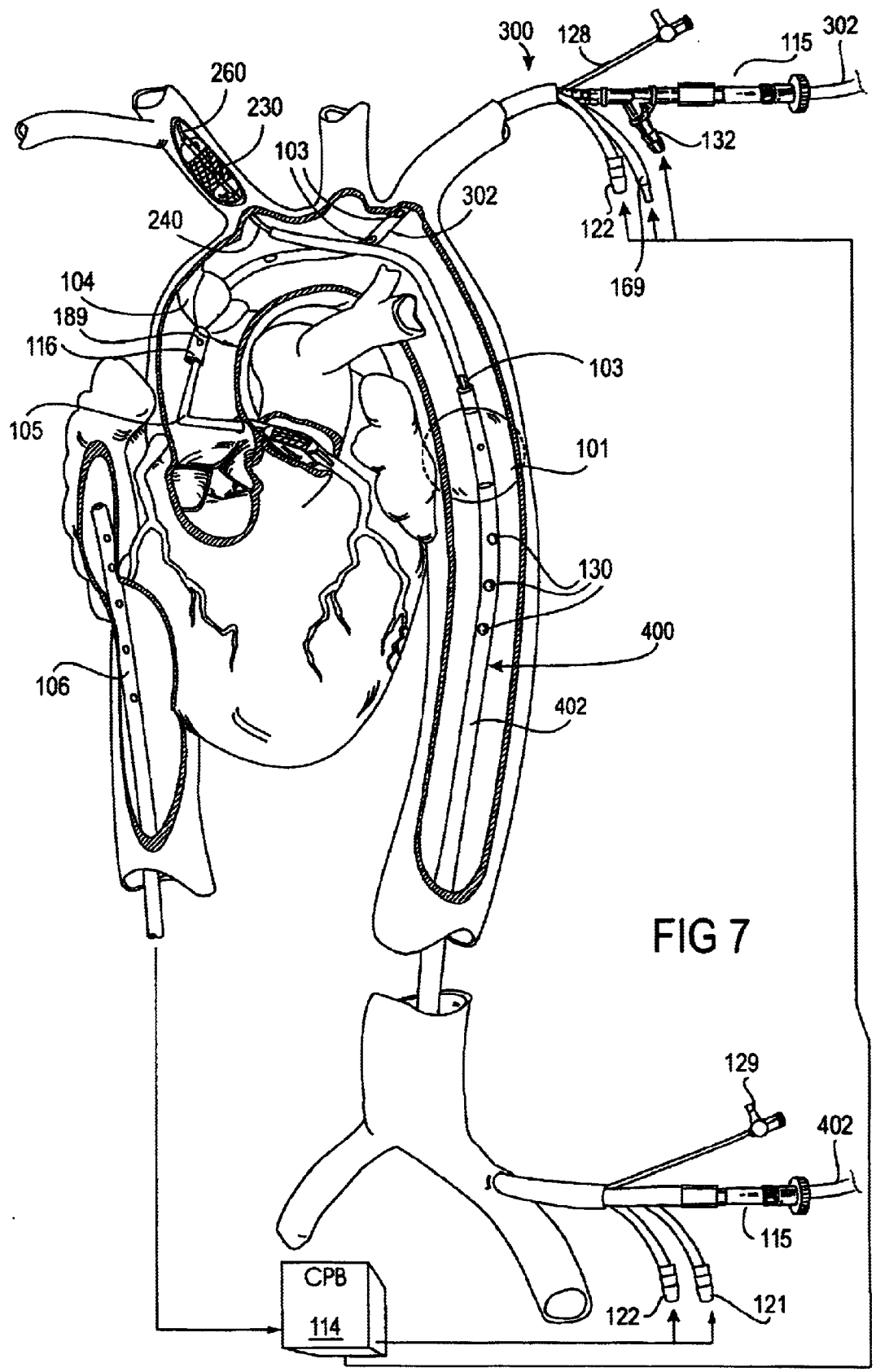
FIG. 7 shows another alternative embodiment of the catheter system of the present invention with a first and second perfusion cannula configured for delivering a therapeutic catheter subsystem and capable of selective perfusion to separate organ systems.

By way of example, FIG. 7 illustrates an embodiment of a system where aortic segmentation and/or perfusion is fulfilled by a first catheter having an upstream occlusion member adapted for occluding the patient's ascending aorta which is expandable from a first elongated catheter shaft. A second catheter having a second elongated catheter shaft has a downstream occlusion member mounted thereon which is sized and configured for occluding the patient's descending aorta. The catheter device for performing a diagnostic or therapeutic catheter procedure within a patient's aorta maybe provided through another peripheral access site, in parallel with the access site of one of the aforementioned catheters or coaxially through either one of the previously mentioned catheters.

One method of using the previously described catheters is to insert a first peripheral arterial cannula 300 in an upper extremity, for example the left or right subclavian artery or axillary artery and place a second peripheral arterial cannula 400 in a lower extremity, for example in the femoral artery. A first upstream occlusion member 104, in this illustrative embodiment in the form of an external flow control valve; is mounted on the first catheter shaft 302. A second flow control member 404, in this illustrative embodiment in the form of an occlusion balloon, is mounted on the second catheter shaft 402. The perfusion functions are fulfilled by the first peripheral arterial cannula 300 which supplies oxygenated blood and/or neuroprotective agents to the arch circulation through arch ports 103, and the second peripheral arterial cannula 400 which supplies oxygenated blood to the corporeal circulation through corporeal ports 130. In addition, the second perfusion cannula 400 can provide for the perfusion functions of both the arch and corporeal circulations which would allow for a low profile cannula design for the first perfusion cannula 300 which would serve as a flow control regulator catheter and or therapeutic catheter delivery catheter with optional cardioplegia delivery and aspiration of the aortic root. A central instrument lumen can be located in either one or both of the peripheral arterial cannulas depending upon the procedure to be performed. In this illustrative embodiment both perfusion cannulas have an instrument lumen. A carotid stent assembly is being placed through the instrument lumenr of the second perfusion catheter 400 and a coronary stent is being placed through the instrument lumen of the first perfusion catheter 300. In addition, either one or both of the occlusion members may be incorporated into the therapeutic/diagnostic catheters as illustrated in connection with FIG. 5A.

Thus, the examples given should only be interpreted as illustrations of some of the preferred embodiments of the invention. It is understood that the figures are examples of illustrative embodiments and any of the catheter systems may be compatible with other catheter systems described in different figures, therefore the full scope of the invention should be determined by the appended claims and their legal equivalents.

What is claimed is:

1. A system for catheter-based procedures comprising:
    a catheter device for performing a diagnostic or therapeutic catheter procedure within a patient; and
    a circulatory support catheter having at least one elongated catheter shaft and having an upstream occlusion member adapted for occluding the patient's ascending aorta and a downstream occlusion member adapted for occluding the patient's descending aorta.

2. The system of claim 1 wherein said upstream occlusion member is an inflatable balloon adapted for occluding the patient's ascending aorta and said downstream occlusion member is an inflatable balloon adapted for occluding the patient's descending aorta.

3. The system of claim 1 wherein said upstream occlusion member is an external catheter flow control valve adapted for occluding the patient's ascending aorta and said downstream occlusion member is an external catheter flow control valve adapted for occluding the patient's descending aorta.

4. The system of claim 1 wherein said upstream occlusion member adapted for occluding the patient's ascending aorta and said downstream occlusion member adapted for occluding the patient's descending aorta are selected from the group consisting of an inflatable balloon and an external catheter flow control valve.

5. The system of claim 1, 2, 3 or 4 wherein said circulatory support catheter further comprises a catheter delivery lumen having an internal diameter sufficient for passage of said catheter device through said catheter delivery lumen.

6. The system of claim 1, 2, 3 or 4 wherein said circulatory support catheter further comprises an arch perfusion lumen having an arch perfusion port located on said elongated catheter shaft between said upstream occlusion member and said downstream occlusion member for perfusing the patient's aortic arch vessels.

7. The system of claim 1, 2, 3 or 4 wherein said circulatory support catheter further comprises a corporeal perfusion lumen having a corporeal perfusion port located downstream of said downstream occlusion member.

8. The system of claim 1, 2, 3 or 4 wherein said circulatory support catheter further comprises a coronary perfusion lumen having a coronary perfusion port located upstream of said upstream occlusion member.

9. The system of claim 1, 2, 3 or 4 wherein said circulatory support catheter further comprises a catheter delivery lumen having an internal diameter sufficient for passage of said catheter device through said catheter delivery lumen, an arch perfusion lumen having an arch perfusion port located on said elongated catheter shaft between said upstream occlusion member and said downstream occlusion member for perfusing the patient's aortic arch vessels, a corporeal perfusion lumen having a corporeal perfusion port located downstream of said downstream occlusion member and a coronary perfusion lumen having a coronary perfusion port located upstream of said upstream occlusion member.

10. The system of claim 1, 2, 3 or 4 wherein said catheter device comprises a catheter selected from the group consisting of an angioplasty catheter, a stent placement catheter, an atherectomy catheter, a valvuloplasty catheter, an electrophysiology catheter, a transmyocardial revascularization catheter, a patent ductus arteriosus closure catheter, a septal defect repair catheter, an intravascular ultrasonic imaging catheter, a laser angioplasty catheter and a laser ablation catheter.

11. A method of performing a catheter based procedure consisting of the steps of:
    (a) occluding a patient's aorta between the patient's coronary arteries and brachiocephalic artery,
    (b) occluding the patient's aorta downstream of the patient's left subclavian artery; and
    (c) performing a therapeutic or diagnostic catheter procedure utilizing a therapeutic or diagnostic catheter.

12. The method of performing a catheter based procedure of claim 11 wherein steps (a) and (b) are performed by:
    inserting a circulatory support catheter into the patient's aorta having at least one elongated catheter shaft, an upstream occlusion member adapted for occluding the patient's ascending aorta and a downstream occlusion member adapted for occluding the patient's descending aorta.

13. The method of performing a catheter based procedure of claim 12 further comprising the steps of:
    delivering said therapeutic or diagnostic catheter through a delivery lumen extending at least in part along the length of said circulatory support catheter and having an internal diameter of sufficient size and diameter for passage of said therapeutic or diagnostic catheter, an arch perfusion lumen having an arch perfusion port located between said upstream occlusion member and said downstream occlusion member for perfusing the patient's aortic arch vessels, a corporeal perfusion lumen within said second elongated catheter shaft having a corporeal perfusion port located downstream of said downstream occlusion member and a coronary perfusion lumen within said first elongated catheter shaft having a coronary perfusion port located upstream of said upstream occlusion member.

14. The method of performing a catheter based procedure of claim 11 wherein step (a) is performed by:
    inserting into the patient's aorta a first catheter having a first elongated catheter shaft and having an upstream occlusion member adapted for occluding the patient's ascending aorta.

15. The method of performing a catheter based procedure of claim 11 wherein step (b) is performed by:
inserting into the patient's aorta a second catheter having a second elongated catheter shaft and having a downstream occlusion member adapted for occluding the patient's descending aorta.

16. The method of performing a catheter based procedure of claim 15 further comprising:
positioning said first catheter and said second catheter coaxially into a patient's aorta.

17. The method of performing a catheter based procedure of claim 15 further comprising:
positioning said first catheter and said second catheter collaterally into a patient's aorta.

18. The method of performing a catheter based procedure of claim 15 further comprising:
positioning said first catheter and said second catheter contalaterally into a patient's aorta.

19. The method of performing a catheter based procedure of claim 15 further comprising:
positioning said first catheter and said second catheter in parallel in a patient's aorta.

20. The method of performing a catheter based procedure of claim 15 further comprising:
inserting said first catheter into a first peripheral artery and inserting said second catheter into a second peripheral artery.

21. The method of performing a catheter based procedure of claim 11 wherein steps (a) and (b) are performed by:
expanding an upstream occlusion member adapted for occluding the patient's ascending aorta mounted on an elongated catheter shaft of said therapeutic or diagnostic catheter; and
expanding a downstream occlusion member adapted for occluding the patient's descending aorta mounted on said elongated catheter shaft of said therapeutic or diagnostic catheter.

22. The method of performing a catheter based procedure of claim 11 wherein steps (a) and (b) are performed by:
inserting said therapeutic or diagnostic catheter into the patient's aorta having at least one elongated catheter shaft, an upstream occlusion member adapted for occluding the patient's ascending aorta and a downstream occlusion member adapted for occluding the patient's descending aorta.

23. The method of performing a catheter based procedure of claim 11 wherein step (a) is performed by inserting said therapeutic or diagnostic catheter into the patient's aorta having an upstream occlusion member adapted for occluding the patient's ascending aorta, and step (b) is performed by inserting into the patient's aorta a circulatory support catheter having a downstream occlusion member adapted for occluding the patient's descending aorta.

24. The method of performing a catheter based procedure of claim 11 wherein step (a) is performed by inserting into the patient's aorta a circulatory support catheter having an upstream occlusion member adapted for occluding the patient's ascending aorta, and step (b) is performed by inserting into the patient's aorta said therapeutic or diagnostic catheter having an downstream occlusion member adapted for occluding the patient's descending aorta.

25. The method of performing a catheter based procedure of claim 11 wherein steps (a) and (b) are performed by:
occluding the patient's ascending and descending aorta with a first and second occlusion balloon.

26. The method of performing a catheter based procedure of claim 11 wherein steps (a) and (b) are performed by:
occluding the patient's ascending and descending aorta with a first and second external catheter flow control valve.

27. The method of performing a catheter based procedure of claim 11 wherein said therapeutic or diagnostic catheter is selected from the group consisting of an angioplasty catheter, a stent placement catheter, an atherectomy catheter, a valvuloplasty catheter, an electrophysiology catheter, a transmyocardial revascularization catheter, a patent ductus arteriosus closure catheter, a septal defect repair catheter, an intravascular ultrasonic imaging catheter, a laser angioplasty catheter and a laser ablation catheter.

28. The method of performing a catheter based procedure of claim 11 further comprising the steps of:
inserting a venous catheter into the patient's venous system.

* * * * *